United States Patent
Ding et al.

(10) Patent No.: US 11,204,408 B2
(45) Date of Patent: *Dec. 21, 2021

(54) SYSTEM AND METHOD FOR MAGNETIC RESONANCE IMAGING

(71) Applicant: SHANGHAI UNITED IMAGING HEALTHCARE CO., LTD., Shanghai (CN)

(72) Inventors: Yu Ding, Houston, TX (US); Renjie He, Houston, TX (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/817,734

(22) Filed: Mar. 13, 2020

(65) Prior Publication Data
US 2020/0209332 A1 Jul. 2, 2020

Related U.S. Application Data

(63) Continuation of application No. 15/638,347, filed on Jun. 29, 2017, now Pat. No. 10,591,569, which is a
(Continued)

(51) Int. Cl.
*G01R 33/565* (2006.01)
*G06F 17/14* (2006.01)
(Continued)

(52) U.S. Cl.
CPC ........... *G01R 33/565* (2013.01); *G01R 23/16* (2013.01); *G01R 33/4818* (2013.01);
(Continued)

(58) Field of Classification Search
CPC .. G01R 33/565; G01R 23/16; G01R 33/4818; G01R 33/5659; G06F 17/14; G06T 7/0012
See application file for complete search history.

(56) References Cited

U.S. PATENT DOCUMENTS 7,282,917 B1 * 10/2007 Brau ................... G01R 33/5611
                                                    324/309
8,354,844 B2 * 1/2013 Zaitsev ............. G01R 33/5611
                                                    324/307
(Continued)

FOREIGN PATENT DOCUMENTS

| CN | 102435966 A | 5/2012 |
| CN | 104166113 A | 11/2014 |
| CN | 105467342 A | 4/2016 |

OTHER PUBLICATIONS

Jackson, John et al., Selection of a Convolution Function for Fourier Inversion Using Gridding, IEEE Transactions on Medical Imaging, 10(3) :473-478, 1991.
(Continued)

*Primary Examiner* — Utpal D Shah
(74) *Attorney, Agent, or Firm* — Metis IP LLC

(57) ABSTRACT

The disclosure relates to a system and method for correcting inhomogeneity in an MRI image. The method may include the steps of: acquiring a first set of k-space data, acquiring a second set of k-space data, generating the convolution kernel of the first set of k-space data based on the first set of k-space data and the second set of k-space data, performing inverse Fourier transform on the convolution kernel of the first set of k-space data to obtain an inversely transformed convolution kernel of the first set of k-space data, and generating a corrector based on the inversely transformed convolution kernel of the first set of k-space data. The method may be implemented on a machine including at least one processor and storage.

20 Claims, 11 Drawing Sheets

Related U.S. Application Data continuation of application No. PCT/CN2017/072659, filed on Jan. 25, 2017.

(51) Int. Cl.
*A61B 5/055* (2006.01)
*G01R 33/48* (2006.01)
*G01R 23/16* (2006.01)
*A61B 5/00* (2006.01)

(52) U.S. Cl.
CPC ......... *G01R 33/5659* (2013.01); *G06F 17/14* (2013.01); *A61B 5/0013* (2013.01); *A61B 5/055* (2013.01); *A61B 5/7257* (2013.01); *A61B 2576/00* (2013.01)

(56) References Cited

U.S. PATENT DOCUMENTS

| | | | | |
|---|---|---|---|---|
| 9,196,062 B2* | 11/2015 | Hwang | ................ | G01R 33/565 |
| 9,389,292 B2* | 7/2016 | Beatty | ................ | G01R 33/5611 |
| 2004/0254447 A1* | 12/2004 | Block | ................ | G01R 33/563 |
| | | | | 600/410 |
| 2012/0286777 A1 | 11/2012 | Frost et al. | | |
| 2013/0279781 A1 | 10/2013 | Ding et al. | | |
| 2014/0340083 A1* | 11/2014 | Zhang | ................ | G01R 33/5611 |
| | | | | 324/309 |
| 2016/0217555 A1 | 7/2016 | Ertel et al. | | |
| 2016/0291106 A1* | 10/2016 | Fuderer | ................ | G01R 33/561 |
| 2017/0146630 A1* | 5/2017 | Huang | ............ | G01R 33/56509 |
| 2018/0246178 A1* | 8/2018 | Wang | ....................... | G01V 3/14 |

OTHER PUBLICATIONS

International Search Report in PCT/CN2017/072659 dated Oct. 11, 2017, 4 pages.

Written opinion in PCT/CN2017/072659 dated Oct. 11, 2017, 4 pages.

Vovk U. et al. A Review of Methods for Correction of Intensity Inhomogeneity in MRI, IEEE Transactions on Medical Imaging, 26(3):405-421, 2007.

Ming Fang et al., A Dual Image Approach for Bias Field Correction in Magnetic Resonance Imaging, Magnetic resonance imaging, 21(2): 121-125, 2003.

First Office Action in Chinese Application No. 201780084516.0 dated Feb. 9, 2021, 20 pages.

* cited by examiner

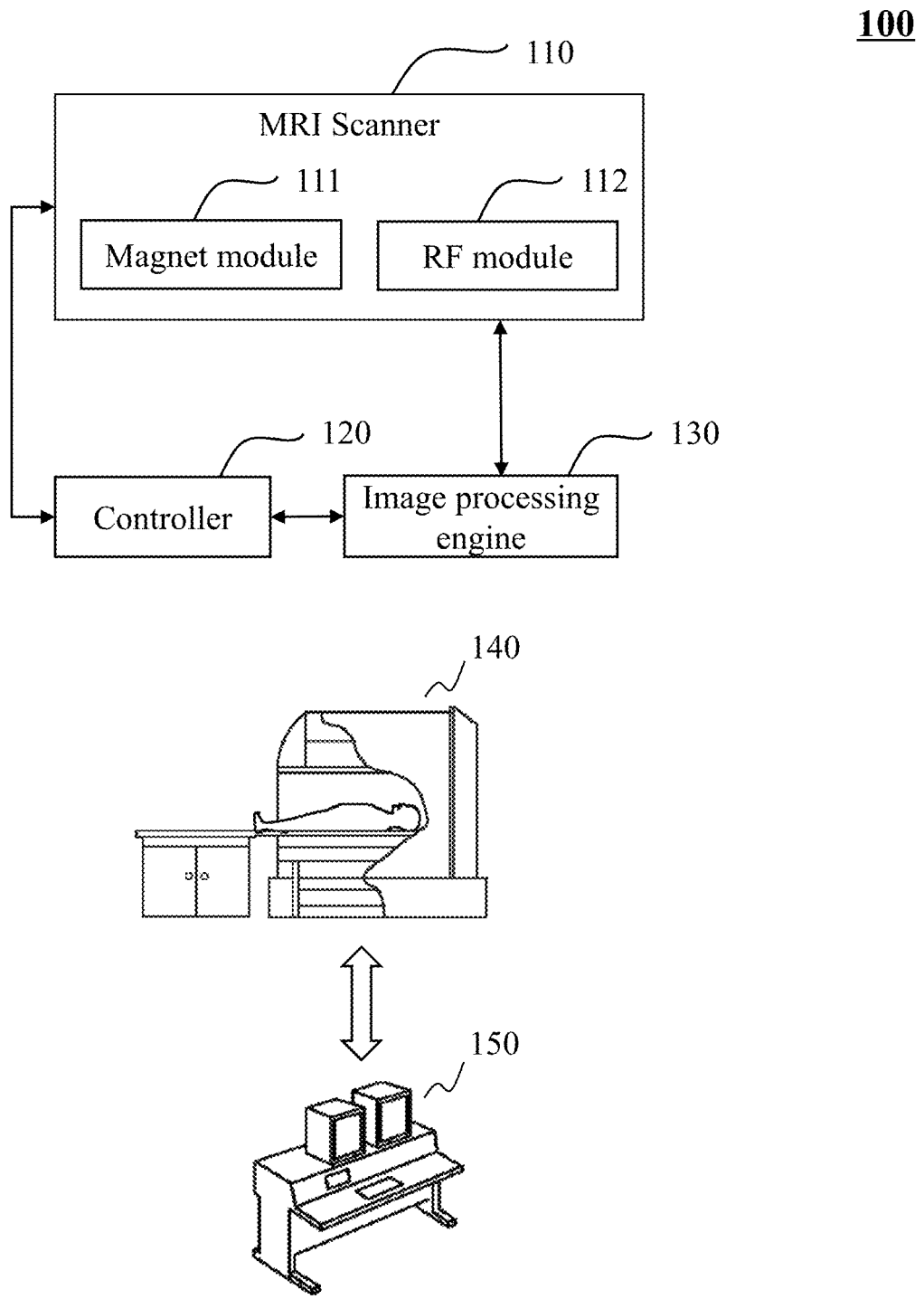
FIG. 1-A

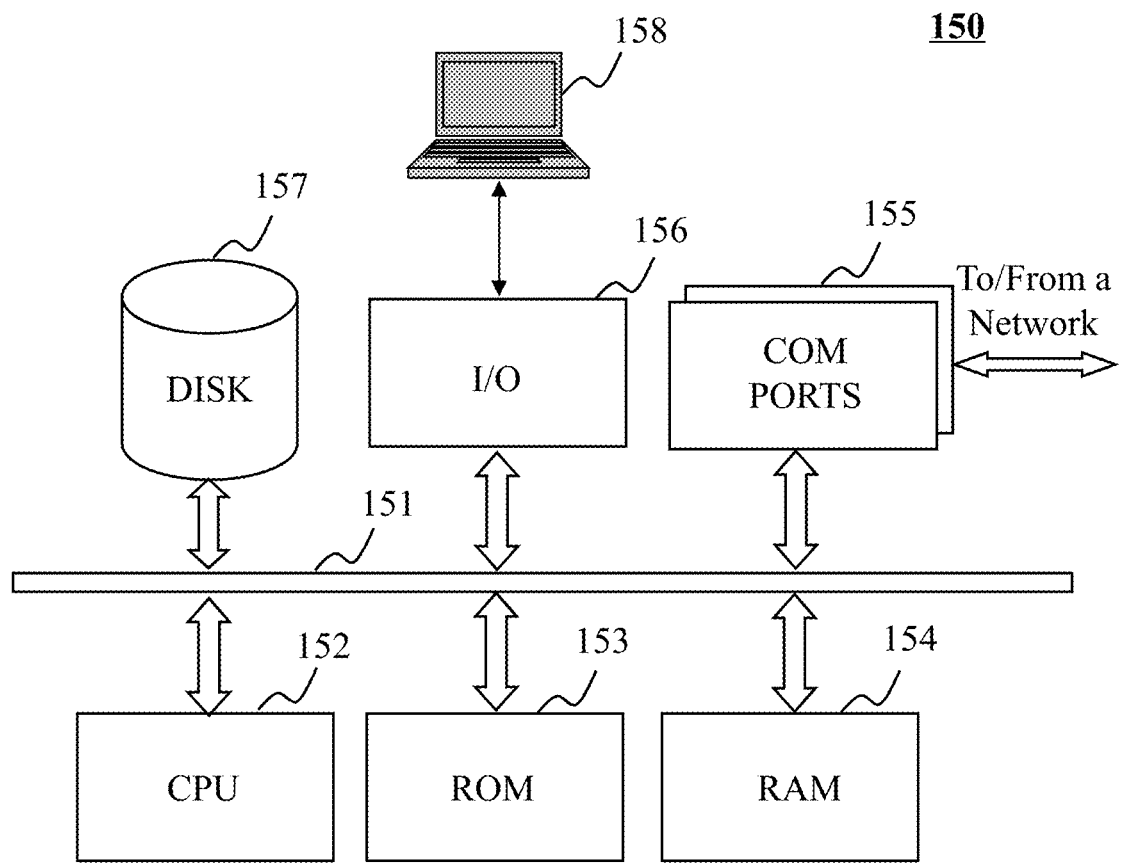
FIG. 1-B

| $a_{n-2,m-2}$ | $a_{n-2,m-1}$ | $a_{n-2,m}$ | $a_{n-2,m+1}$ | $a_{n-2,m+2}$ |
|---|---|---|---|---|
| $a_{n-1,m-2}$ | $a_{n-1,m-1}$ | $a_{n-1,m}$ | $a_{n-1,m+1}$ | $a_{n-1,m+2}$ |
| $a_{n,m-2}$ | $a_{n,m-1}$ | $a_{n,m}$ | $a_{n,m+1}$ | $a_{n,m+2}$ |
| $a_{n+1,m-2}$ | $a_{n+1,m-1}$ | $a_{n+1,m}$ | $a_{n+1,m+1}$ | $a_{n+1,m+2}$ |
| $a_{n+2,m-2}$ | $a_{n+2,m-1}$ | $a_{n+2,m}$ | $a_{n+2,m+1}$ | $a_{n+2,m+2}$ |

910

| $c_{-1,-1}$ | $c_{-1,0}$ | $c_{-1,1}$ |
|---|---|---|
| $c_{0,-1}$ | $c_{0,0}$ | $c_{0,1}$ |
| $c_{1,-1}$ | $c_{1,0}$ | $c_{1,1}$ |

930

| $b_{n-2,m-2}$ | $b_{n-2,m-1}$ | $b_{n-2,m}$ | $b_{n-2,m+1}$ | $b_{n-2,m+2}$ |
|---|---|---|---|---|
| $b_{n-1,m-2}$ | $b_{n-1,m-1}$ | $b_{n-1,m}$ | $b_{n-1,m+1}$ | $b_{n-1,m+2}$ |
| $b_{n,m-2}$ | $b_{n,m-1}$ | $b_{n,m}$ | $b_{n,m+1}$ | $b_{n,m+2}$ |
| $b_{n+1,m-2}$ | $b_{n+1,m-1}$ | $b_{n+1,m}$ | $b_{n+1,m+1}$ | $b_{n+1,m+2}$ |
| $b_{n+2,m-2}$ | $b_{n+2,m-1}$ | $b_{n+2,m}$ | $b_{n+2,m+1}$ | $b_{n+2,m+2}$ |

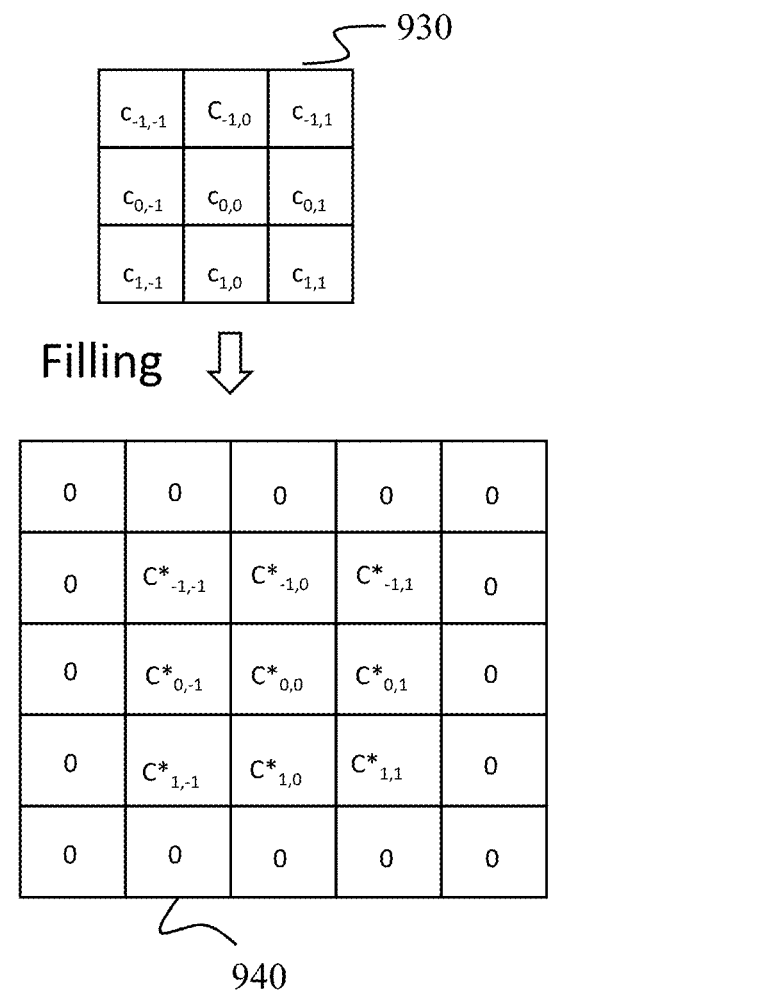
FIG. 9-B

SYSTEM AND METHOD FOR MAGNETIC RESONANCE IMAGING

CROSS-REFERENCE TO RELATED APPLICATIONS

This application is a continuation of U.S. application Ser. No. 15/638,347, filed on Jun. 29, 2017, which is a continuation of International Application No. PCT/CN2017/072659, filed on Jan. 25, 2017, the contents of each of which are hereby incorporated by reference.

TECHNICAL FIELD

The present disclosure generally relates to magnetic resonance imaging (MRI), and more particularly, to a system and method for correcting inhomogeneity in an MRI image.

BACKGROUND

Magnetic resonance imaging (MRI) is a widely used medical technique which produces images of a region of interest (ROI) by exploiting a powerful magnetic field and radio frequency (RF) techniques. During an MRI process, volume coils (for example, body coils) and local coils (for example, surface coils) may acquire MR signals produced by nuclear relaxation inside the subject being examined. Further, the acquired signals may be processed and filled into the k-space, then data in the k-space may be transformed to reconstruct MRI images. However, due to the imperfection of the signal acquisition process, the intensity inhomogeneity in an MRI image may manifest itself as a smooth intensity variation across the image. Thus, a system and method for correcting the intensity inhomogeneity in the MRI images may be proposed.

SUMMARY

In a first aspect of the present disclosure, a system for correcting inhomogeneity in an MRI image is provided. The system may include a storage device and at least one processor. The storage may store instructions, a first set of k-space data relating to a first region of a subject acquired using one or more first coils, a second set of k-space data relating to the first region of subject acquired using one or more second coils, etc. For instance, the one or more first coils and the one or more second coils may include one or more surface coils and one or more body coils, respectively. The processor may be configured to execute the instructions. When executing the instructions, the processor causes the system to perform one or more of the following operations. The convolution kernel of a first set of k-space data may be generated based on the first set of k-space data and the second set of k-space data. Inverse Fourier transform may be performed on the convolution kernel of the first set of k-space data to obtain an inversely transformed convolution kernel of the first set of k-space data. A corrector may be generated based on the inversely transformed convolution kernel of the first set of k-space data. The corrector may be stored in electronic form as a data file. The corrector may be adapted for correcting an image relating to the one or more first coils.

In a second aspect of the present disclosure, a method for correcting inhomogeneity in an MRI image is provided. The method may include one or more of the following operations. A first set of k-space data relating to a first region of a subject may be acquired using one or more first coils. A second set of k-space data relates to the first region of the subject may be acquired using one or more second coils. The convolution kernel of the first set of k-space data may be generated based on the first set of k-space data and the second set of k-space data. Inverse Fourier transform may be performed on the convolution kernel of the first set of k-space data to obtain an inversely transformed convolution kernel of the first set of k-space data. A corrector may be generated based on the inversely transformed convolution kernel of the first set of k-space data. The corrector may be stored in electronic form as a data file. The corrector may be adapted for correcting an image relating to the one or more first coils.

In some embodiments, the subject may be, for example, a human being or another type of animal. In some embodiments, the subject may be a plant or a non-living sample. The first region of the subject may include part of the subject. The one or more first coils may include one or more surface coils. The one or more second coils may include one or more body coils. The first set of k-space data may include a first k-space data set and/or a transformed first image data set. The first k-space data set may include a candidate k-space data set. The candidate k-space data set may be a surface coil k-space data set generated by filling the MR signals acquired by surface coil(s) into a k-space. The MR signals may be acquired by the surface coil(s) during a pre-scan or an imaging scan. The transformed first image data set may be generated by performing Fourier transform on the first image data set. The first image data set may include a candidate image data set. The candidate image data set may be a surface coil image data set generated based on the MR signals acquired by surface coil(s). The MR signals may be acquired by the surface coil(s) during a pre-scan or an imaging scan. In some embodiments, the first image data set may be of a first size. In some embodiments, the first set of k-space data may be of a second size. The second size may relate to the first size.

In some embodiments, the second set of k-space data may include the second k-space data set and/or the transformed second image data set. The second k-space data set may include the reference k-space data set. The reference k-space data set may be generated by filling the MR signals acquired by body coil(s) into a second k-space. The MR signals may be acquired by the body coil(s) during a pre-scan or an imaging scan. The transformed second image data set may be obtained by performing Fourier transform on the second image data set. The second image data set may include the reference image data set. The reference image data set may be a body coil image data set generated based on the MR signals acquired by the body coil(s). In some embodiments, the second image data set may be of the same size as the first image data set. In some embodiments, the second set of k-space data may be of the same size as the first set of k-space data.

In some embodiments, the convolution kernel of the first set of k-space data may be a matrix of coefficients. The convolution kernel of the first set of k-space data may provide information relating to the first k-space data set and/or the first image data set. For example, the convolution kernel of the first set of k-space data may provide information (for example, the coil sensitivity information) relating to the coil(s) that have acquired the MR signals for the generation of the first k-space data set and/or the first image data set.

In some embodiments, the inversely transformed convolution kernel of the first set of k-space data may be generated based on a data set originally filled with zeroes. The complex conjugate of the convolution kernel of the first set of k-space data may be generated. The data set originally filled with zeroes may be populated with the complex conjugate of the convolution kernel of the first set of k-space data at the center. Further, the inverse Fourier transform may be performed on the populated data set to obtain the inversely transformed convolution kernel of the first set of k-space data. In some embodiments, the size of the data set may relate to the size of the first image data set and the size of the second image data set. The first set of k-space data may be corrected based on the corrector. Merely by way of example, the first image data set may be corrected by multiplying the corrector by the first image data set. In some embodiments, a third image data set that was not used to generate the corrector may be acquired by the surface coil(s). In some embodiments, the third image data set may be acquired during an imaging scan. The third image data set may relate to a second region of the subject. In some embodiments, the second region of the subject may be located within the first region of the subject. In some embodiments, the third image data set may be corrected by multiplying the corrector by the third image data set.

In a third aspect of the present disclosure, a method for correcting inhomogeneity in an MRI image is provided. The method may be implemented on a device having a processor and a storage device. The method may include one or more of the following operations. An image data set relating to a region of a subject may be acquired by one or more coils. A first corrector may be obtained based on a convolution kernel of a first set of k-space data. The first set of k-space data may be acquired by the coil(s). The image data set may be corrected using the first corrector. In some embodiments, the first corrector may be obtained by resizing or interpolating a second corrector.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1-A is a block diagram of a magnetic resonance imaging (MRI) system according to some embodiments of the present disclosure;

FIG. 1-B illustrates an exemplary architecture of a computing device according to some embodiments of the present disclosure;

FIG. 9-A illustrates an exemplary diagram illustrating the generation of the convolution kernel of the first set of k-space data; and FIG. 9-B illustrates an exemplary diagram illustrating the process of generating the convolution kernel of the first set of k-space data.

DETAILED DESCRIPTION

Figure 2:
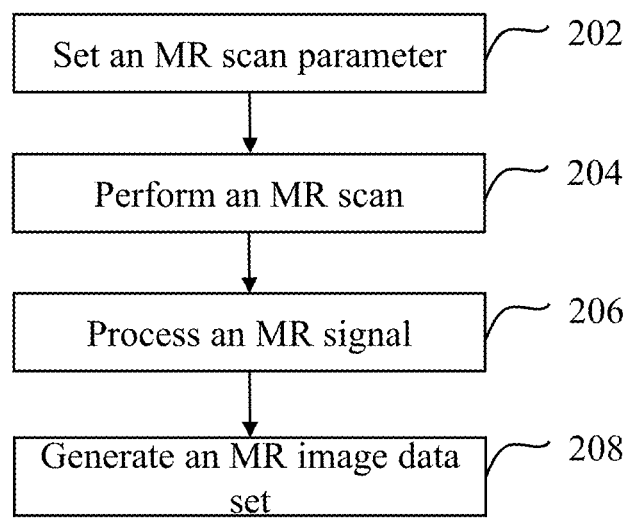
FIG. 2 is a flowchart of an MR scan according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

FIG. 1-A is a block diagram of a magnetic resonance imaging (MRI) system 100 according to some embodiments of the present disclosure. As illustrated, the MRI system 100 may include an MRI scanner 110, a controller 120, a processing module 130, etc. The MRI scanner 110 may include a magnet module 111 and a radio frequency (RF)

module 112. In some embodiments, the MRI scanner 110 may perform a scan on a subject or a region of the subject. The subject may be, for example, a human body or other animal body. For example, the subject may be a patient. The region of the subject may include part of the subject. For example, the region of the subject may include a tissue of the patient. The tissue may include, for example, lung, prostate, breast, colon, rectum, bladder, ovary, skin, liver, spine, bone, pancreas, cervix, lymph, thyroid, spleen, adrenal gland, salivary gland, sebaceous gland, testis, thymus gland, penis, uterus, trachea, skeletal muscle, smooth muscle, heart, etc. In some embodiments, the scan may be a pre-scan for calibrating an imaging scan. In some embodiments, the scan may be an imaging scan for generating an image.

The magnet module 111 may include a main magnet field generator and/or a gradient magnet field generator (not shown in FIG. 1-A). The main magnet field generator may create a static magnetic field BO during a scan. The main magnet may be of various types including, for example, a permanent magnet, a superconducting electromagnet, a resistive electromagnet, etc.

The gradient magnet field generator may generate magnet field gradients on the main magnet field BO in a certain direction, for example, X, Y, and/or Z directions. As used herein, the X, Y and Z direction may represent X, Y and Z axis in a coordinate system. Merely by way of example, the X axis and the Z axis may be in a horizontal plane, the X axis and the Y axis may be in a vertical plane, the Z axis may be along the rotational axis of the gantry. In some embodiments, the X axis, the Y axis, and the Z axis may be specified by the gradient magnet field generator (i.e., gradient coils in the gradient magnet field generator). The gradient magnet field may encode and/or readout the spatial information of the subject (or a region of the subject) located within the MRI scanner 110.

In some embodiments, the magnet module 111 may generate magnet field gradients in a set of directions during a scan. Merely by way of example, the magnet module 111 may generate a first magnet field gradient in a first direction, a second magnet field gradient in a second direction, and a third magnet field gradient in a third direction. In some embodiments, the first, second, and third direction, may be along the X axis, the Y axis, and the Z axis, respectively. In some embodiments, the magnet field gradients along the X axis, the Y axis, and/or the Z axis may correspond to different encoding/readout directions in the k-space (e.g., the direction of the kx axis, the direction of the ky axis, the direction of the kz axis, or any other direction).

The function, size, type, geometry, position, amount, and/or magnitude of the magnet module 111 and/or of the RF module 112 may be determined or changed according to one or more specific conditions. Merely by way of example, the magnet module 111 and the radio frequency (RF) module 112 may be designed to surround a subject (or a region of the subject) to form a tunnel type MRI scanner 110 (i.e. a close-bore MRI scanner 110), or an open MRI scanner 110 (i.e. an open-bore MRI scanner 110). In some embodiments, the RF module 112 may be classified as transmitter coils and/or receiver coils. These RF coils may transmit RF signals to, or receive RF signals from the subject (or a region of the subject). Merely by way of example, the transmitter coils may transmit RF energy to the subject (or a region of the subject) to induce electrical signals in the region of interest. As another example, the receiver coils may pick up RF electromagnetic radiation produced by nuclear relaxation inside the subject (or a region of the subject).

In some embodiments, according to the difference in function and/or size, the RF coils may be classified as volume coils and local coils. In some embodiments, the volume coils may include body coils, birdcage coils, transverse electromagnetic coils, saddle coils, etc. In some embodiments of the present disclosure, the local coils may include solenoid coils, saddle coils, flexible coils, surface coils, etc.

The surface coil may be a coil placed directly over the subject (or a region of the subject). In some embodiments, the surface coil may be a receiver coil configured to receive signals produced by nuclear relaxation inside the subject (or a region of the subject). Merely by way of example, the surface coil may receive a plurality of MR signals during a pre-scan and/or an imaging scan. For example, the surface coil may be placed directly over a region of interest (ROI) of the subject, providing improved signal to noise ratios (SNR) by limiting the spatial extent of the reception. In some embodiments, the surface coil may be a loop of a conducting material. Merely by way of example, the surface coil may be a copper tubing. In some embodiments, the loop may form various shapes. Merely by way of example, the loop may be bent to conform with the body part to be examined. In some embodiments, the radio frequency (RF) module 112 may include one or more surface coils. Merely by way of example, the radio frequency (RF) module 112 may include a plurality of surface coils.

The body coil may be a coil that surrounds the subject (or a region of the subject). Merely by way of example, the body coil may surround the head or the knee of a patient being examined. In some embodiments, the body coil may be a receiver coil configured to receive signals produced by nuclear relaxation inside the subject (or a region of the subject), and/or a transmitter coil configured to transmit RF energy to the subject (or the region of the subject). Merely by way of example, the body coil may receive a plurality of MR signals during a pre-scan and/or an imaging scan.

In some embodiments, the radio frequency (RF) module 112 may include one or more receiver coils. The coils may include surface coils and/or body coils. Merely by way of example, the radio frequency (RF) module 112 may include a first receiver coil and a second receiver coil. Both the first receiver coil and the second receiver coil may be surface coils. As another example, both the first receiver coil and the second receiver coil may be body coils. In some embodiments, the radio frequency (RF) module 112 may include a body coil. Merely by way of example, the radio frequency (RF) module 112 may include a body coil surrounding the patient being examined. As another example, the radio frequency (RF) module 112 may include a surface coil and a body coil.

The controller 120 may control the magnet module 111 and/or the RF module 112 of the MRI scanner 110, the image processing engine 130, etc. Merely by way of example, the controller 120 may control the magnet field gradients in the X direction, the Y direction, and the Z direction. In some embodiments, the controller 120 may receive information from, or send information to the MRI scanner 110, the processing 130, etc. According to some embodiments, the controller 120 may receive commands from, for example, a user, and adjust the magnet module 111 and/or RF module 112 to take images of the subject (or a region of the subject) according to the received commands.

In some embodiments, the controller 120 may include an input/output device to receive commands input from the user (for example, a doctor, a nurse, an imaging specialist, etc.). Merely by way of example, the input/output device may include a video display, a track ball, a mice, a keyboard, a microphone, a touch-sensitive display, a transducer card reader, a magnetic or paper tape reader, a tablet, a stylus, a voice or handwriting recognizer, a biometrics reader, a computer, or any combination thereof.

In some embodiments, the controller 120 may communicate with the image processing engine 130 for exchanging information relating to the operation of the MRI scanner 110 or other parts of the MRI system 100. Control logic (software) and data may be stored in a storage device. The storage device may be a main memory or a secondary storage. The main memory may include a random access memory (RAM), a read only memory (ROM), etc. The secondary storage may include, for example, a hard disk drive and/or a removable storage drive, representing a floppy disk drive, a magnetic tape drive, a compact disk drive, etc. The removable storage drive may read from and/or write data to a removable storage unit in a certain manner. In some embodiments, the storage device may be implemented in the MRI system 100. For example, the storage device may be implemented in the controller 120 and/or the image processing engine 130. In some embodiments, the storage device may be an external storage connected to the MRI system 100. In some embodiments of the present disclosure, the controller 120 may be implemented on a computing device 150 as illustrated in FIG. 1-B and the description thereof, via its hardware, software program, firmware, or a combination thereof.

The image processing engine 130 may process different kinds of information received from different modules. In some embodiments, the image processing engine 130 may communicate with or connect to the MRI scanner 110, the controller 120, etc. To better illustrate the present disclosure, several examples are given below, but the examples do not limit the scope of the present disclosure. For example, in some embodiments, the image processing engine 130 may process MR signals received from the RF module 112 (for example, the surface coil(s) and/or the body coil(s)) and generate one or more MR data sets (for example, k-space data sets, or image data sets) based on these signals. Merely by way of example, the MR signals may be filled into a k-space to generate a k-space data set. In some embodiments, these signals may be received by a plurality of receiver coils. The signals received by a same receiver coil may be filled into a plurality of k-space lines of a same k-space. In some embodiments, a k-space line may be in the form of a data set filled with data points. Merely by way of example, the receiver coils may include a first receiver coil and a second receiver coil. The k-space of the first receiver coil may be a first k-space, the k-space of the second receiver coil may be a second k-space.

Merely by way of example, the first receiver coil may receive a signal A and a signal B; the signal A and the signal B may be filled into a first k-space line and a second k-space line of a first k-space, respectively. In some embodiments, the signal B may be received after the signal A. In some embodiments, the second k-space line may be adjacent to the first k-space line. In some embodiments, the signal A and/or the signal B may be undersampled signals. In some embodiments, the undersampled signals may be signals not fully acquired. Consequently, the first k-space line and the second k-space line of the first k-space may constitute an undersampled k-space data set of the first k-space. In some embodiments, an undersampled k-space data set may be a k-space data set including one or more unknown data points. In some embodiments, the first receiver coil may further receive a signal C and a signal D, the signal C and the signal D may be complete signals. In some embodiments, the signal D may be received after the signal C. In some embodiments, the complete signals may be fully acquired signals. In some embodiments, the signal C and the signal D may be filled into a third k-space line and a fourth k-space line of the first k-space. In some embodiments, the third k-space line may be adjacent to the fourth k-space line. In some embodiments, the third K-space line may be next to the second k-space line. In some embodiments, a plurality of k-space lines may be between the second the k-space line and the third k-space line.

In some embodiments, a calibration data set may be selected from the k-space. In some embodiments, the calibration data set may include a fully-acquired k-space data set that includes no unknown data points. For instance, a portion of the first k-space line and a portion of the second k-space line may constitute a locally complete k-space data set of the first k-space, and a calibration data set. As another example, the third k-space line and the fourth k-space line, or a portion thereof, may constitute a calibration data set. As a further example, a portion of the first k-space line and a portion of the second k-space line, along with a portion of the third k-space line and a portion the fourth k-space line, may constitute a locally complete k-space data set of the first k-space, and a calibration data set. As still a further example, a portion of the second k-space line and a portion of the third k-space line may constitute a locally complete k-space data set of the first k-space, and a calibration data set.

The calibration data set may be used to generate information related to a parameter (for example, the coil sensitivity) relating to the receiver coil(s) (for example, the first receiver coil(s)) that have received the calibration data set. In some embodiments, a synthesizing filter may be generated based on the calibration data set. The synthesizing filter may provide calibration information relating to the receiver coil(s) for calibrating the undersampled data set that correspond to the signals received by the receiver coil(s).

The image processing engine 130 may generate a complete k-space data set based on the undersampled k-space data set and the synthesizing filter. The complete k-space data set may include the calibration data set and a filled-in undesampled k-space data set. In some embodiments, the unknown data points in the originally undersampled k-space data set may be determined to generate the filled-in undersampled k-space data set. Further, in some embodiments, the image processing engine 130 may generate an image data set based on the complete k-space data set.

The image processing engine 130 may generate a data set. The data set may include a candidate data set and/or a reference data set. In some embodiments, the image processing engine 130 may generate the candidate data set based on signals acquired during the pre-scan and/or the imaging scan. The candidate data set may include a first candidate data set and a second candidate data set. Merely by way of example, the image processing engine 130 may generate the first candidate data set based on signals acquired by the surface coil(s) during the pre-scan. As another example, the image processing engine 130 may generate the second candidate data set based on signals acquired by the surface coil(s) during the imaging scan. In some embodiments, the image processing engine 130 may generate the reference data set based on MR signals acquired during the pre-scan and/or the imaging scan. The reference data set may include a first reference data set and a second reference data set. Merely by way of example, the image processing engine 130 may generate the first reference data set based on signals acquired by the body coil(s) during the pre-scan. As another example, the image processing engine 130 may generate the second reference data set based on signals acquired by the body coil(s) during the imaging scan.

In some embodiments, the candidate data set may include a candidate k-space data set and/or a candidate image data set. Merely by way of example, the first candidate data set may include a first candidate k-space data set and/or a first candidate image data set. As another example, the second candidate data set may include a second candidate k-space data set and/or a second candidate image data set. The reference data set may include a k-space reference data set and/or a reference image data set. Merely by way of example, the first reference data set may include a first reference k-space data set and/or a first reference image data set. As another example, the second reference data set may include a second reference k-space data set and/or a second reference image data set. In some embodiments, the image processing engine 130 may generate a candidate k-space data set. The candidate k-space data set may be a surface coil k-space data set. The candidate k-space data set may be an MR k-space data set generated based on signals acquired by one or more surface coils. In some embodiments, the image processing engine 130 may generate a reference k-space data set for the candidate k-space data set. In some embodiments, the reference k-space data set may be a body coil k-space data set. The body coil k-space data set may be an MR k-space data set generated from signals acquired by one or more body coils.

In some embodiments, the image processing engine 130 may generate a candidate image data set. The candidate image data set may be a surface coil image data set. The surface coil image data set may be an MR image data set generated based on signals acquired by one or more surface coils during a pre-scan or an imaging scan. Merely by way of example, the surface coil may receive a first plurality of signals during the pre-scan, based on which the first candidate image data set may be generated. The first plurality of signals may correspond to a pre-scan region of the subject being examined. Merely by way of example, the first plurality of signals may correspond to the subject (for example, the patient).

In some embodiments, the image processing engine 130 may generate a reference image data set for the candidate image data set. In some embodiments, the reference image data set may be a body coil image data set. The body coil image data set may be an MR image data set generated from signals acquired by one or more body coils during a pre-scan or an imaging scan. Merely by way of example, the body coil(s) may receive a second plurality of MR signals during the pre-scan, based on which the reference image data set may be generated. The second plurality of signals may correspond to the pre-scan region of the subject being examined. Further, in some embodiments, the surface coil(s) may receive a third plurality of MR signals during the imaging scan, based on which the second candidate image data set may be generated. The third plurality of signals may correspond to a scan region of the subject being examined. The scan region of the subject may be located within the pre-scan region of the subject. In some embodiments, the body coil(s) may receive a fourth plurality of MR signals during the imaging scan, based on which the second reference image data set may be generated. The fourth plurality signals may correspond to the scan region of the subject being examined.

In some embodiments, a corrector may be generated based on the candidate image data set and the reference image data set. For example, a corrector may be generated based on the first candidate image data set and the first reference image data set. As another example, the corrector may be generated based on the second candidate image data set and the second reference image data set. The generated corrector may be applied to the first candidate image data set and/or the second candidate image data set. In some embodiments, the corrector may be adapted for image intensity normalization. In some embodiments, the generated corrector may be utilized to correct a data set that was used to generate the corrector. Merely by way of example, the second candidate image data set may be corrected by a corrector that was generated based on the second candidate image data set and the second reference image data set. In some embodiments, the generated corrector may be utilized to correct a data set (for example, a third image data set) that was not used to generate the corrector. The third image data set may be generated based on signals acquired by one or more surface coils. Merely by way of example, the second candidate image data set may be corrected by a corrector that was generated based on the first candidate image data set and the first reference image data set.

In some embodiments, the candidate data set (for example, the first candidate data set or the second candidate data set) may have a higher SNR compared to the reference data set (for example, the first reference data set or the second reference data set). In some embodiments, the candidate data set may have a higher intensity inhomogeneity compared to the reference data set. A corrector may be utilized to correct the intensity inhomogeneity in the candidate data set (for example, the first candidate data set or the second candidate data set). In some embodiments, the corrector may be generated based on the candidate data set and the reference data set. Merely by way of example, the corrector may be generated based on the second candidate image data set and the second reference image data set. As another example, the generated corrector may be applied to the first candidate image data set and/or the second candidate image data set. The corrector may be in an image domain. In some embodiments, the image processing engine 130 may generate a corrected image data set based on the corrector. Merely by way of example, the image processing engine 130 may generate the corrected image data set by applying the corrector to the candidate data set (for example, the first candidate data set or the second candidate data set). In some embodiments, the generated corrector may be utilized to correct a data set that was used to generate the corrector. Merely by way of example, the second candidate data set may be corrected by a corrector that was generated based on the second candidate data set and the second reference data set. In some embodiments, the generated corrector may be utilized to correct a data set (for example, the third image data set) that was not used to generate the corrector. The third image data set may be generated based on signals acquired by surface coil(s). Merely by way of example, the second candidate image data set may be corrected by a corrector that was generated based on the first candidate data set and the first reference data set. The corrected image data set may be an intensity weighted image data set. In some embodiments, the corrected image data set may be displayed or otherwise output. In some embodiments, the image processing engine 130 may process data input by the user or an operator and transform the data into specific commands, and supply the commands to the controller 120. In some embodiments of the present disclosure, the image processing engine 130 may be implemented on a computing device 150 as illustrated in FIG. 1-B and the description thereof, via its hardware, software program, firmware, or a combination thereof.

It should be noted that the above description of the MRI system 100 is merely provided for the purposes of illustration, and not intended to limit the scope of the present disclosure. For persons having ordinary skills in the art, multiple variations and modifications may be made under the teachings of the present disclosure. For example, the assembly and/or function of the MRI system 100 may be varied or changed according to specific implementation scenarios. Merely by way of example, some other components may be added into the MRI system 100, such as a patient positioning module, a gradient amplifier module, and other devices or modules. Note that the MRI system 100 may be a traditional or a single-modality medical system, or a multi-modality system including, e.g., a positron emission tomography-magnetic resonance imaging (PET-MRI) system, a remote medical MRI system, and others, etc. However, those variations and modifications do not depart from the scope of the present disclosure.

FIG. 1-B illustrates an exemplary architecture of a computing device 150 according to some embodiments of the present disclosure. In some embodiments, the controller 120, the image processing engine 130, or a portion thereof, or a combination thereof, may be implemented on the computing device 150 via its hardware, software program, firmware, or a combination thereof.

The computing device 150 may include an internal communication bus 151, a central processing unit (CPU) 152, an I/O interface 156, a communication port 155, and one or more memory devices. The internal communication bus 151 may transmit data between the components (152 through 157) of the computing device 150. For example, the MRI data from the disk 157 may be transmitted through internal communication bus 151 to the CUP 152 to generate an image data set.

The central processing unit (CPU) 152 may execute computer instructions. The computer instructions may relate to routines, programs, objects, components, data structures, procedures, modules, etc. In some embodiments, the CPU 152 may process the data or information received from the MRI scanner 110, the controller 120, or any other component of the MRI system 100. In some embodiments, CPU 152 may include one or more processors. The processors may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof. For example, the processors may include a microcontroller to process the MRI data received from the MRI scanner 110 for image reconstruction.

The one or more memory devices may store the data or information received from the MRI scanner 110. In some embodiments, the memory devices may include a disk 157, a random access memory 154 (RAM), a read-only memory 153 (ROM), or the like, or any combination thereof. The disk 157 may be implemented by, for example, a magnetic disk, an optical disk, a floppy disk, an optical disk, or a zip disk, etc. The RAM 154 may be implemented by, for example, a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM 153 may be implemented by, for example, a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the memory devices may store one or more programs and/or instructions to perform exemplary methods described in the present disclosure. For example, the ROM 153 may store a program or an algorithm for reconstructing an MR image based on the MR data.

The computing device 150 may include one or more COM ports 155 connected to a network to furnish data communications. The communication ports (COM ports) 155 may transmit information to or receive information from MRI scanner 110 via a network. In some embodiments, communication ports 155 may include a wired port (e.g., a Universal Serial Bus (USB), a High Definition Multimedia Interface (HDMI), a wireless port (such as a Bluetooth port, an infrared interface, and a WiFi port), or the like, or any combination thereof.

The I/O interface 156 may support information input or output between the computing device 150 and one or more peripherals. In some embodiments, the peripherals may include a terminal, a keyboard, a touch screen, a cursor control device, a remote controller, or the like, or any combination thereof. The terminal may include, for example, a mobile device (e.g., a smart phone, a smart watch, a laptop computer, or the like), a personal computer, or the like, or any combination thereof. For example, the terminal may be implemented by a computer 158, which may be a general purpose computer or a specially designed computer. The cursor control device may include a mouse, a trackball, or cursor direction keys to communicate direction information and command selections to, for example, the image processing engine 130 or control cursor movement on a display device.

The information input and/or output via I/O interface 156 may include programs, software, algorithms, data, text, number, images, voices, or the like, or any combination thereof. For example, the user may input some initial parameters or conditions to initiate an MRI data processing. In some embodiments, the information input via I/O interface 156 may be input via a keyboard, a touch screen, a voice sensor, a motion sensor, a brain monitoring system, or any other devices.

Those skilled in the art will recognize that the present teachings are amenable to a variety of modifications and/or enhancements. For example, although the implementation of various components described herein may be embodied in a hardware device, it may also be implemented as a software only solution, e.g., an installation on an existing server. For example, the image processing engine 130 and/or the controller 120 as disclosed herein may be implemented as a firmware, a software, or a combination thereof.

FIG. 2 is a flowchart of an MR scan according to some embodiments of the present disclosure. In 202, an MR parameter may be set. The MR parameter may relate to an MR scanning, a protocol selection, a signal acquisition, a data processing, a data storage, a data calibration, an image generation, or the like, or any combination thereof. Merely by way of example, the MR parameter may include an image contrast and/or ratio, the region of interest (ROI), slice thickness, an imaging type (e.g., T1 weighted imaging, T2 weighted imaging, proton density weighted imaging, etc.), a spin echo type (spin echo, fast spin echo (FSE), fast recovery FSE, single shot FSE, gradient recalled echo, fast imaging with stead-state procession, and etc.), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. In some embodiments, the MR parameter may be set in the controller 120. In some embodiments, the MR parameter may be set via the computing device 150 through a user interface.

In 204, an MR scan may be performed by, for example, the MRI scanner 110. In some embodiments, an MR parameter including a pulse sequence may be sent to the MRI scanner 110 to generate RF excitation pulses and magnetic field gradients during the MR scan. The pulse sequence may be, for example, a spin echo (SE) sequence, a fast spin echo (FSE) sequence, an ultrashort echo-time (UTE) sequence, a gradient echo (GRE) sequence, etc. Merely by way of example, a radial 3D UTE sequence may be provide to the MRI scanner 110. In some embodiments, the pulse sequence may be sent to the MRI scanner 110 in a form of a timing diagram. In some embodiments, an MR signal may be acquired during the MR scan. In some embodiments, the acquired MR signal may be an analog signal.

In 206, the MR signal acquired during the MR scan may be processed by, for example, the image processing engine 130. The MR signal acquired during the MR scan may be detected or acquired by the surface coil(s) and/or the body coil(s). In some embodiments, various signal processing methods may be applied to process the acquired signal. Merely by way of example, the signal processing methods may include analog-to-digital conversion, linear fitting, 2D Fourier transform (2D FT), fast Fourier transform (FFT), interpolation algorithm, regridding, or the like, or any combination thereof. In some embodiments, the acquired signal may be converted to a set of discrete data. Furthermore, the discrete data may be processed to fill into the k-space to generate a k-space data set. Merely by way of example, the MR signals acquired by a surface coil may be filled into a k-space of the surface coil. As another example, the MR signals acquired by a body coil may be filled into a k-space of the body coil.

The MR signals acquired by the surface coil(s) may be filled into the k-space of the surface coil(s) to generate a candidate k-space data set. In some embodiments, the MR signals acquired by the surface coil(s) may be acquired during a pre-scan and/or an imaging scan. The MR signals acquired by the surface coil(s) during the pre-scan may include the first plurality of MR signals. The MR signals acquired by the surface coil(s) during the imaging scan may include the third plurality of MR signals. Merely by way of example, the first plurality of MR signals may be filled into the k-space of the surface coil(s) to generate the first candidate k-space data set. As another example, the third plurality of MR signals may be filled into the k-space of the surface coil(s) to generate the second candidate k-space data set. The MR signal acquired by the body coil(s) may be filled into the k-space of the body coil(s) to generate a reference k-space data set. In some embodiments, the MR signals acquired by the body coil(s) may be acquired during a pre-scan and/or an imaging scan. The MR signals acquired by the body coil(s) during the pre-scan may include the second plurality of MR signals. The MR signals acquired by the body coil(s) during the imaging scan may include the fourth plurality of MR signals. Merely by way of example, the second plurality of MR signals may be filled into the k-space of the body coil(s) to generate the first reference k-space data set. As another example, the fourth plurality of MR signals may be filled into the k-space of the body coil(s) to generate the second reference k-space data set.

In some embodiments, a corrector may be generated based on the candidate k-space data set and the reference k-space data set. Merely by way of example, the corrector may be generated based on the first candidate k-space data set and the first reference k-space data set. As another example, the corrector may be generated based on the second candidate k-space data set and the second reference k-space data set. Further, in some embodiments, the generator corrector may be configured to correct the candidate k-space data set (for example, the first candidate k-space data set and/or the second candidate k-space data set). In some embodiments, the acquired signal may include undersampled signals and complete signals. In some embodiments, the undersampled signals and the complete signals may be received by a same coil. In some embodiments, the undersampled signals may be filled into a k-space to generate the undersampled k-space data set. In some embodiments, the complete signals may be filled into the k-space to generate the calibration data set. In some embodiments, a synthesizing filter may be generated based on the calibration data set. The calibration data set may be applied to the undersampled k-space data set to generate a complete k-space data set.

In 208, an MR image data set may be generated based on the processed signal. In some embodiments, the image processing engine 130 may be configured to generate the MR image. In some embodiments, the MR image may be generated based on the complete k-space data set. In some embodiments, the image data set may be generated by repeating 202 through 206 for a certain number of times. In some embodiments, the certain number of times may be determined by the MRI system 100 or provided by the user (e.g., a doctor). In some embodiments, the generated image data set may be the candidate image data set, and/or the reference image data set. The candidate image data set may be generated based on the MR signals acquired by the surface coil(s). The reference image data set may be generated based on the MR signals acquired by the body coil(s).

In some embodiments, the generated image data set may be a T1-weighted image data set, a T2-weighted image data set, a PD (proton density)-weighted image data set, an FLAIR (fluid attenuated inversion recovery) image data set, an intensity weighted image data set, or the like. Merely by way of example, the intensity weighted image data set may be generated based on the candidate image data set and the reference image data set. Specifically, the candidate image data set and the reference image data set may be generated based on the processed signals. The corrector configured to correct the intensity inhomogeneity in the candidate image data set may be generated based on the candidate image data set and the reference image data set. Further, the intensity weighted image data set may be generated by correcting the candidate image data set with the corrector. In some embodiments, the intensity weighted image data set may be further processed to generate a report. The intensity weighted image data set and/or the generated report may be output to a related device (e.g., to be printed, to be displayed, or the like).

It should be noted that the above description is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, the process may further include an operation between 204 and 206 for storing the acquired MR signal.

Figure 3:
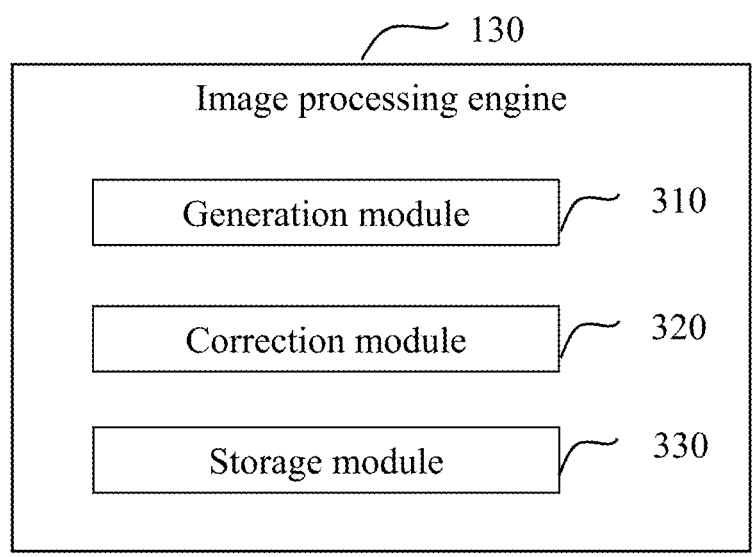
FIG. 3 is a block diagram illustrating an image processing engine according to some embodiments of the present disclosure.

FIG. 3 is a block diagram illustrating the image processing engine 130 according to some embodiments of the present disclosure. The image processing engine 130 as illustrated in FIG. 1-A may process information before, during, or after an imaging procedure. Note that the construction of the image processing engine 130 may have some other variations, and that FIG. 3 is provided for illustration purposes. The image processing engine 130 may be implemented on the computing device 150 including a CPU. The CPU may be a central processing unit (CPU), an application-specific integrated circuit (ASIC), an application-specific instruction-set processor (AS IP), a graphics processing unit (GPU), a physics processing unit (PPU), a microcontroller unit, a digital signal processor (DSP), a field programmable gate array (FPGA), an ARM, or the like, or any combination thereof. As shown in FIG. 3, the image processing engine 130 may include a generation module 310, a correction module 320, and a storage module 330.

The generation module 310 may generate a data set based on the MR signals acquired during the MR scan. The data set may include a k-space data set or an image data set. The MR signals acquired during the MR scan may be acquired by the surface coil(s) and/or the body coil(s). The k-space data set generated may include a candidate k-space data set and/or a reference k-space data set. The image data set generated may include a candidate image data set and/or a reference image data set.

In some embodiments, the generation module 310 may communicate with or connect to the correction module 320, the storage module 330, the controller 120, the MRI scanner 110, etc. In some embodiments, the generation module 310 may process different kinds of information from the MRI scanner 110, or received from the controller 120, provided by a user, etc. The information from the MRI scanner 110 may be a plurality of MR signals of a subject (or a region of the subject). The information from the controller 120 may include information about the MRI scanner 110, the magnet module 111, a patient position (e.g., within an MRI system 100), the RF module 112, or the like, or any combination thereof. In some embodiments, the information may be a patient position, the main and/or gradient magnet intensity, the radio frequency phase and/or amplitude, and so on.

The information from the controller 120 may include information from the user and/or other external resource. Exemplary information from the user may include parameters regarding image contrast and/or ratio, a subject of interest (or a region of the subject of interest), slice thickness, an imaging type (e.g., T1 weighted imaging, T2 weighted imaging, proton density weighted imaging, etc.), T1, T2, a spin echo type (e.g., spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. The generation module 310 may process the data such as magnetic resonance (MR) signals acquired from the subject of interest (or a region of the subject of interest) and process them into a data set. The data set may include a k-space data set and/or an image data set. In some embodiments, the data set may include a candidate data set and/or a reference data set. The candidate data set may be generated based on MR signals acquired by the surface coil(s). In some embodiments, the candidate data set may include a candidate k-space data set and/or a candidate image data set. The reference data set may be generated based on MR signals acquired by the body coil(s). In some embodiments, the reference data set may include a reference k-space data set and/or a reference image data set.

In some embodiments, the generation module 310 may process the data such as magnetic resonance (MR) signals acquired from the subject of interest (or a region of the subject of interest) and process them into a k-space data set. In some embodiments, the generation module 310 may fill the MR signals into a k-space to generate a k-space data set. Merely by way of example, the generation module 310 may fill the MR signals acquired by the surface coil(s) into the k-space of the surface coil(s) to generate the candidate k-space data set. As another example, the generation module 310 may fill the MR signals acquired by the body coil(s) into the k-space of the body coil(s) to generate the reference k-space data set.

In some embodiments, the generation module 310 may process the data such as magnetic resonance (MR) signals acquired from the subject of interest (or a region of the subject of interest) and reconstruct them into an MR image data set. In some embodiments, the generation module 310 may convert analog MR signals to digital MR signals. In some embodiments, one or more parameters may be set before or during the conversion, e.g., voltage, current, rate, sampling frequency, or the like, or a combination thereof. The converted MR signals may be stored in the storage module 330. In some embodiments, the generation module 310 may spatially decode an MR signal that has been spatially encoded by the magnetic field(s). The intensity or magnitude of the signal, and other properties such as a phase number, a relaxation time (T1 or T2), magnetization transfer, or the like, may be ascertained.

The generation module 310 may employ different kinds of imaging reconstruction techniques for the image data set reconstruction procedure. Exemplary reconstruction techniques may include Fourier reconstruction, constrained image data set reconstruction, regularized image data set reconstruction in parallel MRI, or the like, or a variation thereof, or any combination thereof. Merely by way of example, the generation module 310 may acquire the MR signals detected by the surface coil(s) and the body coil(s) from the MRI scanner 110 during the pre-scan, and generate a candidate image data set and a reference image data set based on the MR signals acquired by the surface coil(s) and the body coil(s), respectively.

In some embodiments, the generated candidate data set and the reference data set may be transmitted to the correction module 320. The candidate data set may include a candidate k-space data set and/or a candidate image data set.

In some embodiments, the generation module 310 may perform Fourier transform on the candidate image data set to obtain a transformed candidate image data set. The transformed candidate image data set may be in the k-space domain. Merely by way of example, the transformed candidate image data set may be in the form of a data set. As another example, the transformed candidate image data set may be in the form of a matrix. In some embodiments, the generation module 310 may perform the Fourier transform on the reference image data set to obtain a transformed reference image data set. Merely by way of example, the generation module 310 may perform Fourier transform on the first reference image data set to obtain a transformed first reference image data set. As another example, the generation module 310 may perform Fourier transform on the second reference image data set to obtain a transformed second reference image data set. The transformed reference image data set (for example, the transformed first reference image data set and/or the transformed second reference image data set) may be in the k-space domain. Merely by way of example, the transformed reference image data set may be in the form of a data set. As another example, the transformed reference image data set may be in the form of a matrix.

In some embodiments, the transformed candidate image data set and the transformed reference image data set may be transmitted to the correction module 320. Merely by way of example, the transformed first candidate image data set and the transformed first reference image data set may be transmitted to the correction module 320. As another example, the transformed second candidate image data set and the transformed second reference image data set may be transmitted to the correction module 320.

The correction module 320 may correct the candidate image data set based on the image data or k-space data received from the generation module 310 and/or the storage module 330. In some embodiments, the correction module 320 may receive the candidate k-space data set, the reference k-space data set, the candidate image data set, the reference image data set, the transformed candidate image data set, the transformed reference image data set, or any combination thereof, from, for example, the generation module 310 and/or the storage module 330.

The correction module 320 may generate a corrector to correct an error or artifact (for example, the intensity inhomogeneity) in the candidate data set. Merely by way of example, the correction module 320 may be configured to perform image intensity normalization. In some embodiments, the correction module 320 may generate the corrector based on the candidate data set and the reference data set. The candidate data set may include the candidate k-space data set and/or the candidate image data set. The reference data set may include the reference k-space data set and/or the reference image data set. The reference data set may have a less intensity inhomogeneity compared to the candidate data set. In some embodiments, the correction module 320 may generate the corrector based on the candidate k-space data set and the reference k-space data set. Merely by way of example, the correction module 320 may generate the corrector based on a candidate k-space data set and a reference k-space data set.

In some embodiments, the correction module 320 may correct the candidate k-space data set based on the generated corrector. Merely by way of example, the correction module 320 may correct a second candidate k-space data set using the corrector generated based on a first candidate k-space data set and a first reference k-space data set. As another example, the correction module 320 may correct the second candidate k-space data set based on the corrector generated based on the second candidate k-space data set and a second reference k-space data set. In some embodiments, the correction module 320 may generate the corrector based on the candidate image data set and the reference image data set. In some embodiments, the correction module 320 may utilize the generated corrector to correct a data set that was used to generate the corrector. Merely by way of example, the correction module 320 may correct the second candidate data set based on a corrector that was generated based on the second candidate data set and the second reference data set. In some embodiments, the correction module 320 may utilize the generated corrector to correct a data set (for example, the third image data set) that was not used to generate the corrector. The third image data set may be generated based on signals acquired by surface coil(s). Merely by way of example, the correction module 320 may correct the second candidate image data set based on a corrector that was generated based on the first candidate data set and the first reference data set. In some embodiments, the correction module 320 may generate the corrector based on the difference between the candidate image data set and the reference image data set. For instance, the difference may be indicated by the division of the candidate image data set by the reference image data set, or the division of the reference image data set by the candidate image data set. Merely by way of example, the correction module 320 may generate the corrector based on the difference between the candidate image data set and the reference image data set.

In some embodiments, the correction module 320 may generate the corrector based on the transformed candidate image data set and the transformed reference image data set. Merely by way of example, the correction module 320 may generate the corrector based on the transformed first candidate image data set and the transformed first reference image data set. As another example, the correction module 320 may generate the corrector based on the transformed second candidate image data set and the transformed second reference image data set. In some embodiments, the transformed candidate image data set and the transformed reference image data set may be generated by the generation module 310.

In some embodiments, the transformed candidate image data set and the transformed reference image data set may be generated by the correction module 320, based on the candidate image data set and the reference image data set, respectively. Further, in some embodiments, the correction module 320 may correct the candidate image data set based on the corrector. A corrected image data set may be generated. Merely by way of example, the correction module 320 may correct the candidate image data set by multiplying the candidate image data set with the corrector.

The storage module 330 may store the information that may be used by the generation module 310 and/or the correction module 320. The information may include programs, software, algorithms, data, text, number, images and some other information. These examples are provided here for illustration purposes, and not intended to limit the scope of the present disclosure. Algorithms stored in the storage module 330 may include recursion, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof. In some embodiments, the storage module 330 may store MR signals generated by the generation module 310. In some embodiments, the storage module 330 may store the candidate data set (for example, the first candidate data set and/or the second candidate data set) and the reference data set transmitted by the generation module 310. In some embodiments, the storage module 330 may store the corrected image data set transmitted by the correction module 320.

It should be noted that the above description of the image processing engine 130 is merely provided for the purposes of illustration, and not intended to limit the scope of the present disclosure. For persons having ordinary skills in the art, multiple variations or modifications may be made under the teachings of the present disclosure. For example, the assembly and/or function of processing unit may be varied or changed. In some embodiments, the generation module 310 and the correction module 320 may share one storage module 330. While in some embodiments, the generation module 310 and the correction module 320 may have their own storage blocks, respectively. However, those variations and modifications do not depart from the scope of the present disclosure.

Figure 4:
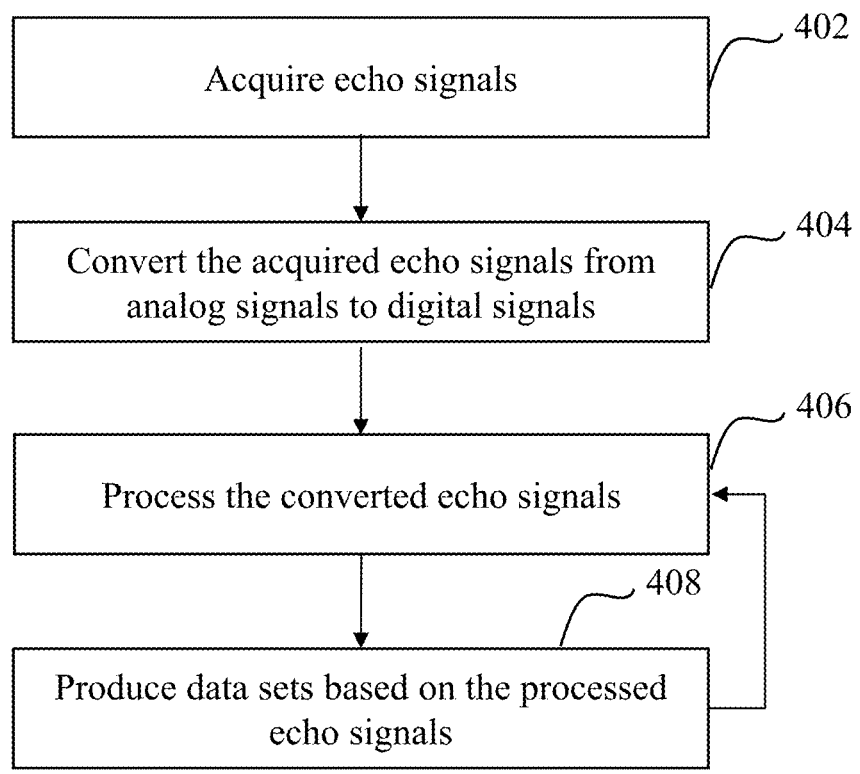
FIG. 4 is a flowchart illustrating a process for processing MR signals according to some embodiments of the present disclosure.

FIG. 4 is a flowchart illustrating a process for processing MR signals according to some embodiments of the present disclosure. In some embodiments, the MR signals may be processed by the generation module 310.

In 402, echo signals may be acquired. The echo signals may be acquired by the MRI scanner 110, or from the storage module 330, or an external resource including, for example, a floppy disk, a hard disk, a wired terminal, a wireless terminal, or the like, or any combination thereof. The echo signals may be detected by the surface coil(s) and/or the body coil(s). The echo signals acquired may be phase encoded, and/or frequency encoded. The echo signals may be acquired from a plurality of shots of a RF pulse sequence. The acquired echo signals may be analog or digital. In some embodiments, acquired analog echo signals may be converted to digital signals in 404. The digitized echo signals may include a plurality of data points, in which each data point may have a specific spatial frequency (i.e., a specific phase and a specific frequency). Further, a data point digitized from an echo signal may be a complex number with a real part and an imaginary part. Alternately, a data point may be defined as having one or more factors or features, e.g., amplitude, phase, or the like. In some embodiments, the amplitude and phase of a data point may be determined by a trigonometric relation. In some embodiments, the digitized echo signals may be stored in the storage module 330 of the image processing engine 130, or an external storage medium including, for example, a floppy disk, a hard disk, a wired terminal, a wireless terminal, or the like, or any combination thereof.

Then the echo signals may be processed in 406. The processing of the echo signals may include a Fourier transform, conversion of the data in the Cartesian coordinate system to data in the polar coordinate system, or vice versa (e.g., conversion of data with real and imaginary parts and data with amplitude and phase components, or vice versa), etc. In some embodiments, the processing may be performed to correct the echo signals. The processing of the echo signals may include weighting operation, averaging, optimization, data filtering, data screening, or the like, or a combination thereof.

The processed echo signals may be used to produce an MR data set in 408. In some embodiments, the MR data set may include a k-space data set and/or an image data set. In some embodiments, the echo signals may be filled into the k-space to generate a k-space data set. The k-space data set may include the candidate k-space data set and/or the reference k-space data set. In some embodiments, the echo signals may be filled into the k-space, processed based on one or more algorithms, and an image data set may be reconstructed. In some embodiments, the echo signals may be filled into the k-space to generate an undersampled k-space data set. The undersampled k-space data set may include at least one unknown data point. In some embodiments, the MR image data set may be the candidate image data set and/or the reference image data set (for example, the first reference image data set and/or the second reference image data set). In some embodiments, the MR image data set may be generated based on the undersampled k-space data set. An exemplary method for generating the MR image data set based on the undersampled k-space data set may be found in PCT Application No. PCT/CN2017/072658, entitled "SYSTEM AND METHOD FOR IMAGE RECONSTRUCTION," filed on even date the entire contents of which are hereby incorporated by reference. In some embodiments, the MR image data set may be corrected. An exemplary method for reducing or removing an intensity inhomogeneity in an MR image data set may be found in U.S. application Ser. No. 15/344,757, entitled "IMAGE RECONSTRUCTION SYSTEM AND METHOD IN MAGNETIC RESONANCE IMAGING" filed on Nov. 7, 2016 the entire contents of which are hereby incorporated by reference.

It should be noted that the above description of the flowchart in FIG. 4 is merely provided for the purposes of illustration, and not intended to limit the scope of the present disclosure. For persons having ordinary skills in the art, multiple variations or modifications may be made under the teachings of the present disclosure. For example, the storage of the echo signals in 406 may be not necessary. Alternatively, an image storage operation may be added after 408. As another example, 406 may be integrated with 408. However, those variations and modifications do not depart from the scope of the present disclosure.

Figure 5:
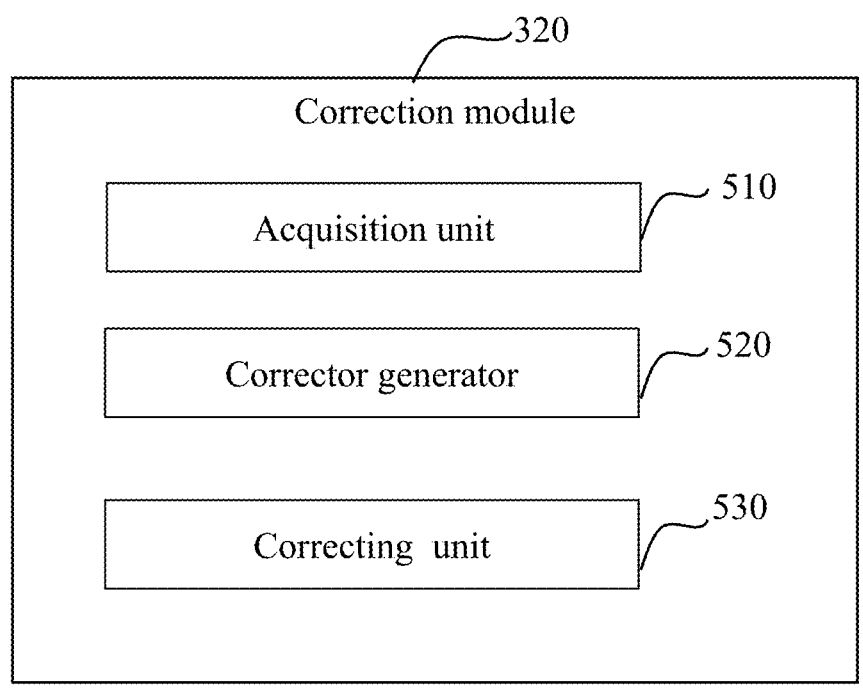
FIG. 5 is a block diagram illustrating a correction module according to some embodiments of the present disclosure.

FIG. 5 is a block diagram illustrating the correction module 320 according to some embodiments of the present disclosure. As illustrated in FIG. 5, the correction module 320 may include an acquisition unit 510, a corrector generator 520, and a correcting unit 530.

The acquisition unit 510 may connect to or communicate with the generation module 310, the storage module 330, and/or the corrector generator 520. In some embodiments, the acquisition unit 510 may receive image data and/or k-space data from the generation module 310 and/or the storage module 330. The k-space data may include the k-space data set. Merely by way of example, the k-space data set may include the candidate k-space data set, and/or the reference k-space data set. The image data may include an image data set. Merely by way of example, the image data set may include the candidate image data set, and/or the reference image data set. Merely by way of example, the acquisition unit 510 may receive the candidate k-space data set, the reference k-space data set, the candidate image data set, the reference image data set, the transformed candidate image data set, and/or the transformed reference image data set from the generation module 310.

In some embodiments, the acquisition unit 510 may transmit the received image data and/or k-space data to the corrector generator 520. Merely by way of example, the acquisition unit 510 may transmit a transformed candidate image data set and a transformed reference image data set received from the generation module 310 to the corrector generator 520, based on which the corrector may be generated. As another example, the acquisition unit 510 may transmit a candidate k-space data set and a reference k-space data set received from the generation module 310 to the corrector generator 520, based on which the corrector may be generated.

The corrector generator 520 may generate a corrector. In some embodiments, the corrector may correct the intensity inhomogeneity in the candidate data set (for example, the first candidate data set and/or the second candidate data set). In some embodiments, the corrector may be in the image domain. Merely by way of example, the corrector may be in the form of a data set. As another example, the corrector may be in the form of a matrix.

The corrector generator 520 may correct the candidate data set based on the candidate data set and the reference data set. The candidate data set and the reference data set may be in the image domain or the k-space domain. In some embodiments, the corrector generator 520 may generate the corrector based on the candidate image data set and the reference image data set. Merely by way of example, the corrector generator 520 may generate the corrector based on a candidate image data set and a reference image data set. In some embodiments, the correction generator 520 may generate the corrector based on the difference between the candidate image data set and the reference image data set. For instance, the difference may be indicated by the division of the candidate image data set by the reference image data set, or the division of the reference image data set by the candidate image data set. Merely by way of example, the correction generator 520 may generate the corrector based on the difference between a candidate image data set and a reference image data set.

In some embodiments, the corrector generator 520 may generate the corrector based on a transformed candidate image data set and the transformed reference image data set. For example, the corrector generator 520 may perform Fourier transform on the candidate image data set to obtain the transformed candidate image data set. The corrector generator 520 may perform the Fourier transform on the reference image data set to obtain transformed reference image data set. Further, in some embodiments, the corrector generator 520 may generate the corrector based on the transformed candidate image data set and the transformed reference image data set. Merely by way of example, the corrector generator 520 may perform Fourier transform on a candidate image data set and a reference image data set to obtain the transformed candidate image data set and the transformed reference image data set, respectively. The corrector generator 520 may generate the corrector based on the transformed candidate image data set and the transformed reference image data set.

For example, the corrector may be a matrix generated based on the convolution kernel of the transformed candidate image data set. The convolution kernel may be generated based on the transformed candidate image data set and the transformed reference image data set. In some embodiments, the corrector generator 520 may generate the corrector based on the candidate k-space data set and the reference k-space data set. For example, the corrector may be a matrix generated based on the convolution kernel of a candidate k-space data set; the convolution kernel may be generated based on the candidate k-space data set and the reference k-space data set. In some embodiments, the generated corrector may be further sent to the correcting module.

The correcting unit 530 may correct the candidate data set based on the corrector. In some embodiments, the correcting unit 530 may utilize the corrector to correct a data set (for example, a third image data set) that was not used to generate the corrector. Merely by way of example, the correcting unit 530 may correct a second candidate data set based on the corrector generated based on a first candidate data set and a first reference data set. In some embodiments, the correcting unit 530 may utilize the corrector to correct a data set that was used to generate the corrector. For example, the correcting unit 530 may correct a second candidate data set based on the corrector generated based on the second candidate data set and a second reference data set. The corrector may be in the image domain. In some embodiments, the correcting unit 530 may resize the corrector to have a size related to the size of the image data set to be corrected. Merely by way of example, the correcting unit 530 may resize the corrector by tailoring or interpolating the corrector. In some embodiments, the correcting unit 530 may correct a candidate image data set by multiplying the candidate image data set with the resized corrector.

It should be noted that the above description of the correction module 320 is merely provided for the purposes of illustration, and not intended to limit the scope of the present disclosure. For persons having ordinary skills in the art, multiple variations and modifications may be made under the teachings of the present disclosure. For example, the function of the acquisition unit 510 may be integrated with the function of the corrector generator 520.

Figure 6:
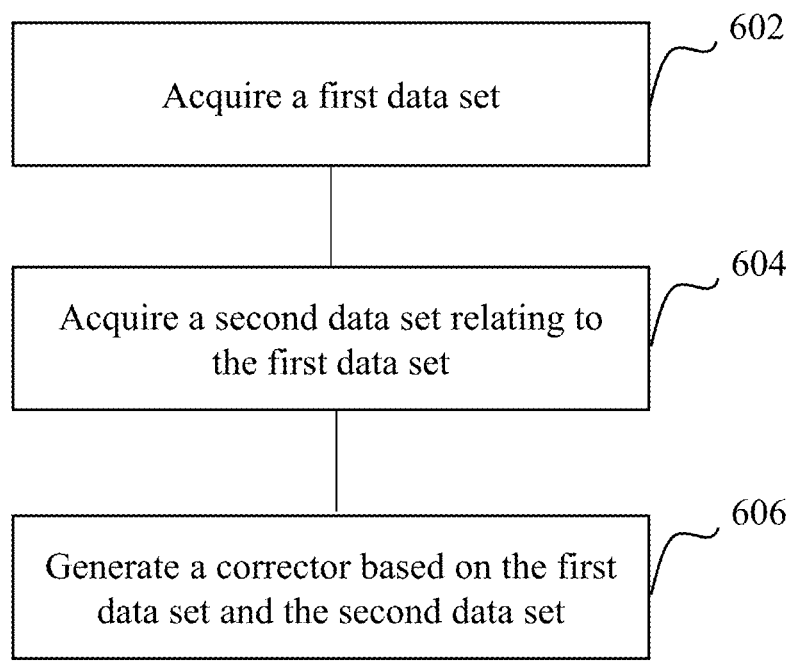
FIG. 6 illustrates an exemplary process for generating a corrector according to some embodiments of the present disclosure.

FIG. 6 illustrates an exemplary process for generating a corrector according to some embodiments of the present disclosure.

In 602, a first data set may be acquired. The first data set may be generated based on signals acquired by one or more surface coils during a pre-scan or an imaging scan. The first data set may be in the k-space domain or the image domain. In some embodiments, the first data set may be acquired by the acquisition unit 510. In some embodiments, the first data set may include a first candidate data set and/or a second candidate data set. The first candidate data set may include a first candidate k-space data set and/or a first candidate image data set. The second candidate data set may include a second candidate k-space data set and/or a second candidate image data set. In some embodiments, the first data set may include a first k-space data set and/or a first image data set. The first k-space data set may include the candidate k-space data set (for example, the first candidate k-space data set and/or the second candidate k-space data set). The candidate k-space data set may be generated by filling the MR signals acquired by the surface coils into a k-space. The first image data set may include the candidate image data set (for example, the first candidate image data set and/or the second candidate image data set). The first data set may be a surface coil data set generated based on the MR signals acquired by the surface coil(s). The surface coil(s) may be placed over the subject being examined, and receive signals corresponding to a certain region (for example, the heart, the lung, etc.) of the subject. Merely by way of example, the first candidate data set may represent a pre-scan region (for example, the heart, the lung, etc.) of the subject. As another example, the second candidate data set may represent a scan region of the subject. In some embodiments, the scan region of the subject may be located within the pre-scan region of the subject.

In 604, a second data set relating to the first data set may be acquired. The second data set may be generated based on signals acquired by one or more body coils during a pre-scan or an imaging scan. The second data set may be in the k-space domain or the image domain. In some embodiments, the second data set relating to the first data set may be acquired by the acquisition unit 510. In some embodiments, the second data set may include a first reference data set and/or a second reference data set. The first reference data set may include a first reference k-space data set and/or a first reference image data set. The second reference data set may include a second reference k-space data set and/or a second reference image data set. In some embodiments, the second data set may include a second k-space data set and a second image data set. The second k-space data set may include the reference k-space data set (for example, a first reference k-space data set and/or a second reference k-space data set). The reference k-space data set may be generated by filling the MR signals acquired by the body coil(s) into the k-space of the body coil(s). The second image data set may include the reference image data set (for example, a first reference image data set and/or a second reference image data set). The second data set may be a body coil data set generated based on the MR signals acquired by the body coil(s). The body coil(s) may surround the subject or a region of the subject being examined, and receive signals corresponding to the subject and/or a region of the subject. In some embodiments, the second data set may relate to the same region (for example, the heart, the lung, etc.) of the subject as the first image data set. Merely by way of example, the first reference data set may represent the pre-scan region of the subject. As another example, the second reference data set may correspond to the scan region of the subject. In some embodiments, the second data set and the first data set may be acquired simultaneously. In some embodiments, the second data set and the first data set may be acquired one after another.

In 606, a corrector may be generated based on the first data set and the second data set. In some embodiments, the corrector may be generated by the corrector generator 520. The corrector may be in the image domain. The first data set may be in a k-space domain or in an image domain. Merely by way of example, the first data set may include the first k-space data set (for example, the first candidate k-space data set and/or the second candidate k-space data set) and/or the first image data set (for example, the first candidate image data set and/or the second candidate image data set). The second data set may include the second k-space data set (for example, the first reference k-space data set and/or the second reference k-space data set) and/or the second image data set (for example, the first reference image data set and/or the second reference image data set). In some embodiments, the corrector may be generated based on a difference between the first k-space data set and the second k-space data set. For example, the corrector may be a matrix generated based on the convolution kernel of the first k-space data set; the convolution kernel may be generated based on the first k-space data set and the second k-space data set. In some embodiments, the corrector may be generated based on the difference between the first image data set and the second image data set. In some embodiments, the difference may be indicated by the division of the candidate image data set by the reference image data set, or the division of the reference image data set by the candidate image data set. In some embodiments, the corrector may be generated based on the transformed first image data set (for example, the transformed first candidate image data set or the transformed second candidate image data set) and the transformed second image data set (for example, the transformed first reference image data set or the transformed second reference image data set). Merely by way of example, the corrector may be generated based on the convolution kernel of the transformed first image data set.

The corrector may be configured to correct the first image data set (for example, the first candidate image data set and/or the second candidate image data set). In some embodiments, the corrector may be resized to have a size related to the size of the first image data set (for example, the first candidate image data set or the second candidate image data set), the first image data set (for example, the first candidate image data set or the second candidate image data set) may be corrected based on the resized corrector. Merely by way of example, the corrector may be tailored and/or interpolated. In some embodiments, the first image data set may be corrected by multiplying the first image data set with the corrector.

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, 602 and 604 may be performed sequentially at an order other than that described above in connection with FIG. 6. Alternatively, 602 and 604 may be performed concurrently.

Figure 7:
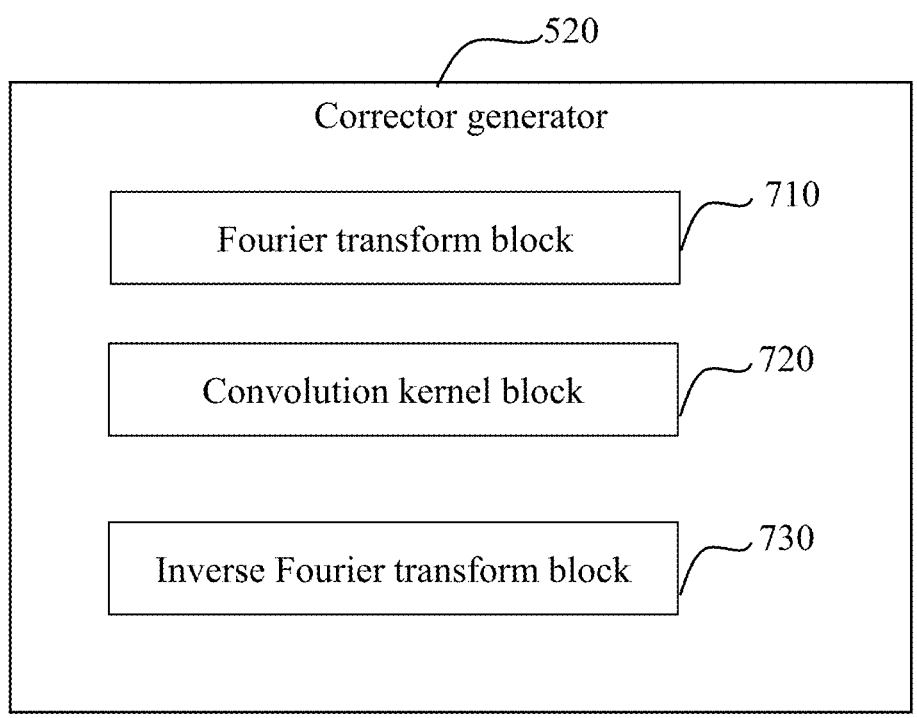
FIG. 7 is a block diagram illustrating a corrector generator according to some embodiments of the present disclosure.

FIG. 7 is a block diagram illustrating the corrector generator 520 according to some embodiments of the present disclosure. As illustrated in FIG. 7, the corrector generator 520 may include a Fourier transform block 710, a convolution kernel block 720, and an inverse Fourier transform block 730.

The Fourier transform block 710 may perform Fourier transform on the MR image data sets received from the acquisition unit 510. In some embodiments, the Fourier transform may decompose a signal based on the frequencies of the signal. The Fourier transform may include, for example, a continuous Fourier transform, a discrete Fourier transform, a discrete-time Fourier transform, a Fourier series, and a circular Fourier transform, or any combination thereof. Merely by way of example, the Fourier transform block 710 may perform Fourier transform on the first image data set and/or the second image data set. The first image data set may include the candidate image data set, for example, the surface coil image data set. Merely by way of example, the first image data set may include the first candidate image data set and/or the second candidate image data set. The second image data set may include the reference image data set, for example, the body coil image data set. Merely by way of example, the second image data set may include the first reference image data set and/or the second reference image data set.

In some embodiments, the Fourier transform block 710 may convert the MR image data sets to the k-space domain by way of Fourier transform. In some embodiments, the Fourier transform block 710 may generate the transformed candidate image data set and the transformed reference image data set by performing the Fourier transform on the first image data set and the second image data set, respectively. Merely by way of example, the Fourier transform block 710 may generate the transformed first candidate image data set and the transformed first reference image data set by performing Fourier transform on the first candidate image data set and the first reference image data set, respectively. As another example, the Fourier transform block 710 may generate the transformed second candidate image data set and the transformed second reference image data set by performing Fourier transform on the second candidate image data set and the second reference image data set, respectively. In some embodiments, the transformed candidate image data set and the transformed reference image data set may be provided to the convolution kernel block 720.

The convolution kernel block 720 may generate a convolution kernel based on the data received from the Fourier transform block 710 and/or the acquisition unit 510. The convolution kernel may be the convolution kernel of the first k-space data set or the convolution kernel of the transformed first image data set. In some embodiments, the convolution kernel of the transformed first image data set (or the convolution kernel of the first k-space data set) may provide information relating to the first image data set (or the first k-space data set). For example, the convolution kernel of the transformed first image data set (or the convolution kernel of the first k-space data set) may provide information relating to the coil(s) that have received the MR signals for the generation of the first image data set (or the first k-space data set). For example, the convolution kernel of the transformed first image data set (or the convolution kernel of the first k-space data set) may reveal information regarding the sensitivity (for example, intensity sensitivity) of the surface coil(s). In some embodiments, the convolution kernel of the transformed first image data set (or the convolution kernel of the first k-space data set) may be a matrix of coefficients. The size of the matrix may be set by the user (for example, a doctor, a nurse, an imaging specialist, etc.). For example, the convolution kernel of the transformed first image data set (or the convolution kernel of the first k-space data set) may be a 3×3 matrix.

The convolution kernel block 720 may generate the convolution kernel of the transformed first image data set based on the transformed first image data set (for example, the transformed first candidate image data set and/or the transformed second candidate image data set) and the transformed second image data set (for example, the transformed first reference image data set and/or the transformed second reference image data set) received from the Fourier transform block 710. The convolution kernel block 720 may generate the convolution kernel of the first k-space data set based on the first k-space data set and the second k-space data set received from the acquisition unit 510. In some embodiments, the generated convolution kernel may be provided to the inverse Fourier transform block 730.

The inverse Fourier transform block 730 may perform the inverse Fourier transform on the convolution kernel of the transformed first image data set (or the convolution kernel of the first k-space data set) received from the convolution kernel block 720. The inverse Fourier transform is an inverse transform of the Fourier transform. In some embodiments, the inverse Fourier transform block 730 may generate the complex conjugate of the convolution kernel of the transformed first image data set (or the complex conjugate of the convolution kernel of the first k-space data set). In some embodiments, the inverse Fourier transform block 730 may populate a data set filled with zeroes with the complex conjugate of the convolution kernel of the transformed first image data set (or the complex conjugate of the convolution kernel of the first k-space data set) to obtain an overwritten data set. Merely by way of example, the inverse Fourier transform block 730 may acquire an original data set filled with zeroes. In some embodiments, the inverse Fourier transform block 730 may populate the center part of the original data set filled with zeroes with the complex conjugate of the convolution kernel of the transformed first image data set (or the complex conjugate of the convolution kernel of the first k-space data set). In some embodiments, the inverse Fourier transform block 730 may perform inverse Fourier transform on the overwritten data set.

It should be noted that the above description of the corrector generator 520 is merely provided for the purposes of illustration, and not intended to limit the scope of the present disclosure. For persons having ordinary skills in the art, multiple variations and modifications may be made under the teachings of the present disclosure. For example, the assembly and/or function of the corrector generator 520 may be varied or changed according to specific implementation scenarios. Merely by way of example, the corrector generator 520 may include a storage block, the storage block may store the data transmitted by the Fourier transform block 710, the convolution kernel block 720, and/or the inverse Fourier transform block 730.

Figure 8:
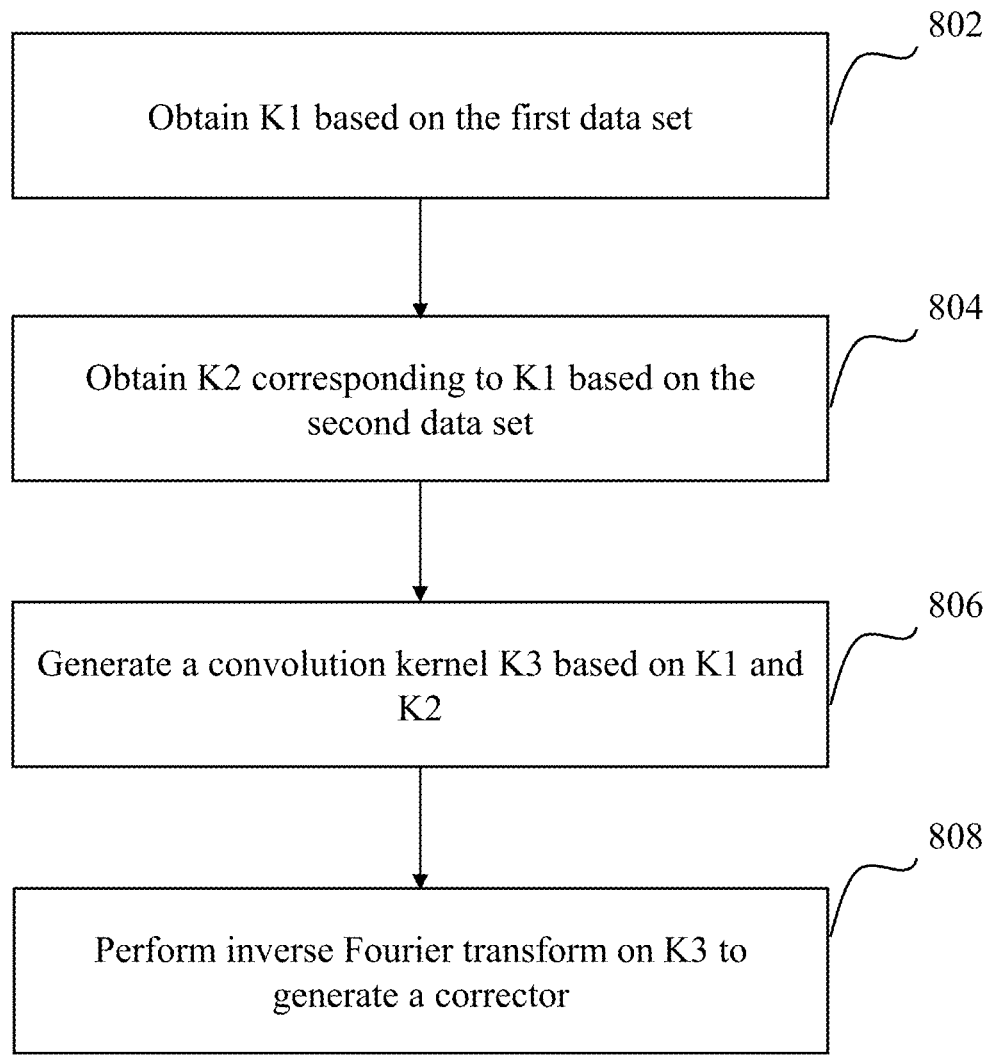
FIG. 8 illustrates an exemplary process for generating the corrector according to some embodiments of the present disclosure.

FIG. 8 illustrates an exemplary process for generating the corrector according to some embodiments of the present disclosure.

In 802, a first set of k-space data (K1) may be obtained. The first set of k-space data may be generated based on signals acquired by surface coil(s) during a pre-scan or an imaging scan. In some embodiments, the first set of k-space data may include the first k-space data set and/or the transformed first image data set. The first k-space data set may include the candidate k-space data set (for example, the first candidate k-space data set and/or the second candidate k-space data set). The first image data set may include the candidate image data set (for example, the first candidate image data set and/or the second candidate image data set). The transformed first image data set may include the transformed candidate image data set (for example, the transformed first candidate image data set and/or the transformed second candidate image data set). Merely by way of example, Fourier transform may be performed on the first image data set to obtain the first set of k-space data. The Fourier transform block 710 may perform Fourier transform on the first image data set. In some embodiments, the Fourier transform may decompose a signal based on the frequencies of the signal up. The Fourier transform may include, for example, a continuous Fourier transform, a discrete Fourier transform, a discrete-time Fourier transform, a Fourier series, and a circular Fourier transform, or any combination thereof.

In 804, a second set of k-space data (K2) may be obtained. The second set of k-space data may be generated based on signals acquired by one or more body coils during a pre-scan or an imaging scan. In some embodiments, the second set of k-space data may include the second k-space data set and/or the transformed second image data set. The second k-space data set may include the reference k-space data set (for example, the first reference k-space data set and/or the second reference k-space data set). The second image data set may include the reference image data set (for example, the first reference image data set and/or the second reference image data set). The transformed second image data set may include the transformed reference image data set (for example, the transformed first reference image data set and/or the transformed second reference image data set). Merely by way of example, Fourier transform may be performed on the second image data set to obtain the second set of k-space data. The Fourier transform block 710 may be used to perform Fourier transform on the second image data set. In some embodiments, the second image data set may have the same size as the first image data set. Merely by way of example, the first reference image data set may have the same size as the first candidate image data set. As another example, the second reference image data set may have the same size as the second candidate image data set. In some embodiments, the first image data set and the second image data set may be acquired simultaneously.

In 806, the convolution kernel of the first set of k-space data (K3) may be generated based on the first set of k-space data and the second set of k-space data. The convolution kernel of the first set of k-space data may provide information relating to the first data set. For example, the convolution kernel of the first set of k-space data may provide information relating to the coil(s) that have acquired the MR signals for the generation of the first data set. For example, the convolution kernel of the first set of k-space data may reveal information regarding the sensitivity (for example, intensity sensitivity) of the surface coil(s). In some embodiments, the convolution kernel of the first set of k-space data may be a matrix of coefficients. The size of the matrix may be set by the user (for example, a doctor, a nurse, an imaging specialist, etc.). The convolution kernel of the first set of k-space data may be generated based on the first set of k-space data and the second set of k-space data. FIG. 9-A illustrates a diagram illustrating the generation of an exemplary convolution kernel of the first set of k-space data based on the first set of k-space data and the second set of k-space data. As illustrated in FIG. 9-A, a matrix 910 may represent the first set of k-space data, a matrix 920 may represent the second set of k-space data, a matrix 930 may represent the convolution kernel of the first set of k-space data generated based on the first set of k-space data and the second set of k-space data, in which $$b_{n,m} = \Sigma_{i=-1}^{1} \Sigma_{j=-1}^{1} a_{n+i,m+j} c_{i,j}. \tag{1}$$

In Equation (1), $a_{n+i,m+j}$ may represent a certain data point in the first set of k-space data, $b_{n,m}$ may represent a certain data point in the second set of k-space data, n or m may denote the row number and the column number in the first set of k-space data or the second set of k-space data, i or j may denote an integer ranging from −1 to 1. In some embodiments, n may be equal to m. It should be noted here that, in some embodiments, according to the present disclosure, i or j may be a number larger than 1 or smaller than −1.

In 808, inverse Fourier transform may be performed on the convolution kernel of the first set of k-space data to generate the corrector. The inverse Fourier transform is an inverse transform of the Fourier transform. In some embodiments, the inverse Fourier transform block 730 may perform the inverse Fourier transform on the convolution kernel of the first set of k-space data. The corrector may be the inversely transformed convolution kernel of the first set of k-space data. In some embodiments, the inversely transformed convolution kernel of the first set of k-space data may be generated occupying the data set filled with zero. Merely by way of example, the data set filled with zero may be acquired, the complex conjugate of the convolution kernel of the first set of k-space data may be generated. The data set filled with zero may be overwritten with the complex conjugate of the convolution kernel of the first set of k-space data at the center. Further, the inverse Fourier transform may be performed on the overwritten data set to obtain the inversely transformed convolution kernel of the first set of k-space data. In some embodiments, the data set filled with zeroes may have a size related to the size of the first image data set and the size of the second image data set. Merely by way of example, the data set filled with zeroes may have the same size as the first set of k-space data. In some embodiments, the corrector may be resized to have the same size as the first image data set through tailoring or interpolating. In some embodiments, the first image data set may be corrected by multiplying the resized corrector with the first image data set.

FIG. 9-B illustrates a diagram illustrating an exemplary process of generating the convolution kernel of the first set of k-space data. The matrix 930 may represent the convolution kernel of the first set of k-space data, the matrix 940 may represent the data set generated by overwriting an original data set filled with zeroes with the complex conjugate of the convolution kernel of the first set of k-space data. In some embodiments, the first image data set may be corrected by multiplying the inversely transformed overwritten data set (or referred to as, the inversely transformed convolution kernel of the first set of k-space data) with the first image data set.

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For example, the process may further include an operation between 804 and 806 for storing the acquired k-space data.

It should be noted that although the method has been described in the context of mitigating or eliminating the inhomogeneities caused by the receiver coils, it may also be used for mitigating or eliminating inhomogeneities caused by the transmitter coils.

It should be noted that the above description is merely provided for the purposes of illustration, and not intended to limit the scope of the present disclosure. The image producing procedures in the present disclosure may be effective in reducing, removing or eliminating other types of motion artifacts including, for example, the vascular pulsation, heart movement, and random motion of the subject being scanned, or the like, or any combination thereof. The image producing procedures in the present disclosure may be applied to whole body MR imaging, and the images produced may have clearer structural details.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method for correcting a target image implemented on at least one machine, each of which has at least one processor and at least one storage device, the method comprising:
   obtaining the target image, the target image being reconstructed based on a target data set;
   obtaining a corrector; and
   reducing intensity inhomogeneity of the target image by correcting the target image using the corrector, wherein the corrector includes a matrix generated based on an inverse Fourier transform of a convolution kernel estimated from a first k-space data set acquired by a first coil and a second k-space data set acquired by a second coil, the second k-space data set having less intensity inhomogeneity than the first k-space data set.

2. The method of claim 1, wherein the correcting the target image using the corrector comprises:
   in response to determining that a size of the corrector is different from a size of the target image, resizing the corrector before correcting the target image using the corrector.

3. The method of claim 2, wherein the resizing the corrector before correcting the target image using the corrector comprises:
   resizing the corrector by tailoring or interpolating the corrector such that the size of the corrector is the same as the size of the target image.

4. The method of claim 1, wherein the correcting the target image using the corrector comprises:
   correcting the target image by multiplying the target image by the corrector.

5. The method of claim 1, wherein the corrector is generated according to a process including:

obtaining the first k-space data set acquired by the first coil;

obtaining the second k-space data set acquired by the second coil;

generating the convolution kernel based on the first k-space data set and the second k-space data set;

generating an inversely transformed convolution kernel by performing an inverse Fourier transform on the convolution kernel; and generating the corrector based on the inversely transformed convolution kernel.

6. The method of claim 5, wherein the performing an inverse Fourier transform on the convolution kernel includes:

generating a complex conjugate of the convolution kernel;

providing an initial data set filled with zeroes;

populating the initial data set with the complex conjugate of the convolutional kernel; and performing the inverse Fourier transform on the populated data set.

7. The method of claim 6, wherein a size of the initial data set is associated with a size of the first k-space data set or the second k-space data set.

8. The method of claim 5, wherein the generating the corrector based on the inversely transformed convolution kernel comprises:

in response to determining that a size of the inversely transformed convolution kernel is different from a size of the target image, resizing the inversely transformed convolution kernel such that the size of the inversely transformed convolution kernel is the same as the size of the target image; and designating the resized inversely transformed convolution kernel as the corrector.

9. The method of claim 5, wherein the generating the corrector based on the inversely transformed convolution kernel comprises:

designating the inversely transformed convolution kernel as the corrector.

10. The method of claim 5, wherein the obtaining the first k-space data set acquired by the first coil comprises:

acquiring a first image data set associated with the first coil; and obtaining the first k-space data set by performing a Fourier transform on the first image data set.

11. The method of claim 5, wherein the obtaining the second k-space data set acquired by the second coil comprises:

acquiring a second image data set associated with the second coil; and obtaining the second k-space data set by performing a Fourier transform on the second image data set.

12. The method of claim 1, wherein the first coil includes a surface coil.

13. The method of claim 1, wherein the second coil includes a body coil.

14. The method of claim 1, wherein the target data set is acquired by the first coil.

15. The method of claim 1, wherein the target data set, the first k-space data set, and the second k-space data set are associated with a same subject or a same region of the subject.

16. The method of claim 1, wherein the first k-space data set and the second k-space data set are associated with a same subject, and the target data set is associated with a region of the subject.

17. The method of claim 1, wherein the first k-space data set and the second k-space data set are acquired during a pre-scan.

18. The method of claim 1, wherein the first k-space data set and the second k-space data set are of a same size.

19. A system for correcting a target image, comprising:

at least one storage device storing a set of instructions; and at least one processor in communication with the storage device, wherein when executing the set of instructions, the at least one processor is configured to cause the system to perform operations including:

obtaining the target image, the target image being reconstructed based on a target data set;

obtaining a corrector; and reducing intensity inhomogeneity of the target image by correcting the target image using the corrector, wherein the corrector includes a matrix generated based on an inverse Fourier transform of a convolution kernel estimated from a first k-space data set acquired by a first coil and a second k-space data set acquired by a second coil, the second k-space data set having less intensity inhomogeneity than the first k-space data set.

20. A non-transitory computer readable medium, comprising at least one set of instructions for correcting a target image, wherein when executed by one or more processors of a computing device, the at least one set of instructions causes the computing device to perform a method, the method comprising:

obtaining the target image, the target image being reconstructed based on a target data set;

obtaining a corrector; and reducing intensity inhomogeneity of the target image by correcting the target image using the corrector, wherein the corrector includes a matrix generated based on an inverse Fourier transform of a convolution kernel estimated from a first k-space data set acquired by a first coil and a second k-space data set acquired by a second coil, the second k-space data set having less intensity inhomogeneity than the first k-space data set.

* * * * *